United States Patent
Dumont D'Ayot et al.

(10) Patent No.: US 8,678,224 B2
(45) Date of Patent: Mar. 25, 2014

(54) INSERT FOR RECEPTACLE CONTAINING SOLID PRODUCTS TO BE DISSOLVED

(75) Inventors: Francois Dumont D'Ayot, Lyons (FR); Paul Gastauer, Hong Kong (CN); Philippe Laffay, Sainte Foy les Lyon (FR)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 36 days.

(21) Appl. No.: 13/260,092

(22) PCT Filed: Mar. 30, 2010

(86) PCT No.: PCT/EP2010/054252
§ 371 (c)(1),
(2), (4) Date: Dec. 7, 2011

(87) PCT Pub. No.: WO2010/115787
PCT Pub. Date: Oct. 14, 2010

(65) Prior Publication Data
US 2012/0067898 A1    Mar. 22, 2012

(30) Foreign Application Priority Data
Apr. 8, 2009 (FR) ..................... 09 52299

(51) Int. Cl.
B65D 1/36 (2006.01)
B65D 25/04 (2006.01)
B65D 85/00 (2006.01)
B65D 6/40 (2006.01)

(52) U.S. Cl.
USPC ........... 220/507; 220/500; 220/501; 220/503; 220/553; 220/555; 220/601

(58) Field of Classification Search
USPC ........ 220/500, 501, 503, 507, 553, 555, 601, 220/661; 206/219, 221
See application file for complete search history.

(56) References Cited

U.S. PATENT DOCUMENTS 4,479,989 A * 10/1984 Mahal .................... 428/35.5
6,572,268 B2 * 6/2003 Ichikawa ................ 383/120

(Continued)

FOREIGN PATENT DOCUMENTS

DE    197 37 747 A1    2/1998
DE    10152105 A1      5/2003

(Continued)

OTHER PUBLICATIONS

International Search Report of PCT/EP2010/054252, mailing date Jun. 21, 2010.

*Primary Examiner* — Anthony Stashick
*Assistant Examiner* — Madison L Poos
(74) *Attorney, Agent, or Firm* — Westerman, Hattori, Daniels & Adrian, LLP

(57) ABSTRACT

An insert for a receptacle intended to contain a concentrated product in solid or liquid form includes a main part (1) formed by a base (2) extended on the edge by a wall (3) perpendicular to the base, with an opening (4) formed in the base. A receptacle with such an insert is also provided. In order to enable emptying the receptacle entirely without leaving dead spaces in which the products to be solubilized may accumulate, the face of the base (2) intended to be in the receptacle after assembly is concave at the opening, so that the opening is at the bottom of a trough (6). This avoids corners in which the liquid would not circulate sufficiently, and prevents solid product from accumulating elsewhere than in the trough, so that it is always subjected to the flow of liquid.

22 Claims, 3 Drawing Sheets

(56) References Cited

U.S. PATENT DOCUMENTS

| | | | |
|---|---|---|---|
| 8,114,061 B2* | 2/2012 | Brandl et al. | 604/408 |
| 2006/0079827 A1 | 4/2006 | Jensen et al. | |
| 2007/0225673 A1* | 9/2007 | Brehm et al. | 604/408 |
| 2009/0143758 A1 | 6/2009 | Okiyama | |
| 2012/0152787 A1* | 6/2012 | Reiter et al. | 206/486 |

FOREIGN PATENT DOCUMENTS

| | | |
|---|---|---|
| EP | 1084691 A2 | 3/2001 |
| EP | 2005934 A2 | 12/2008 |
| WO | 00/19961 A1 | 4/2000 |
| WO | 2006/042016 A2 | 4/2006 |

* cited by examiner

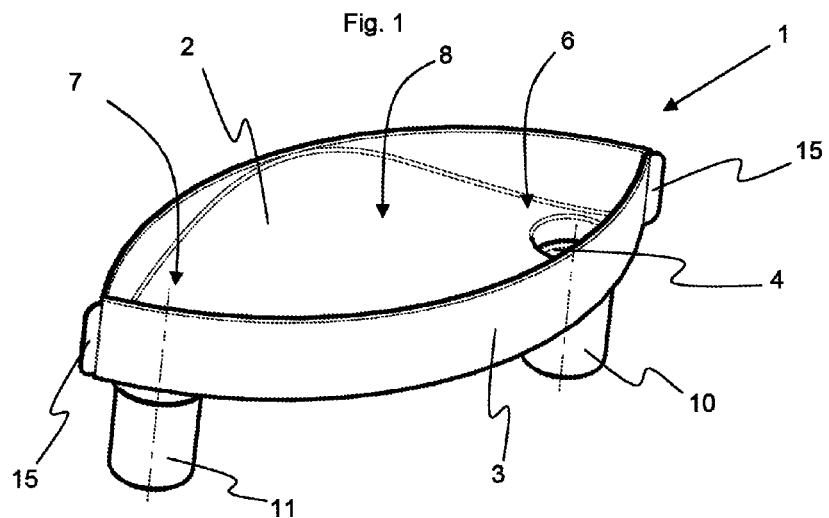
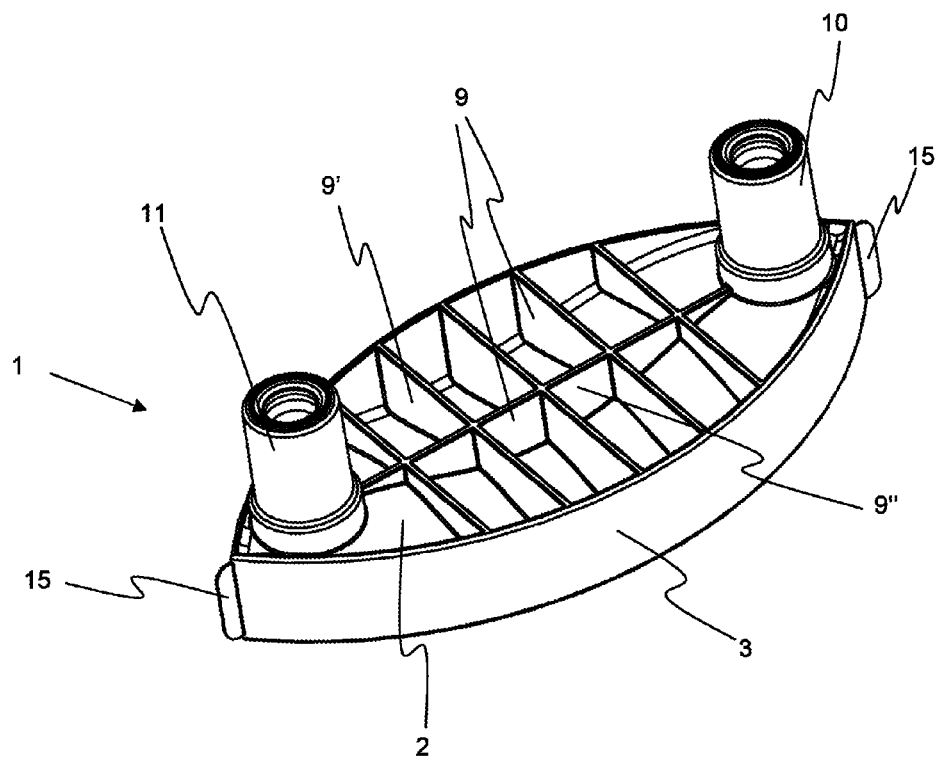

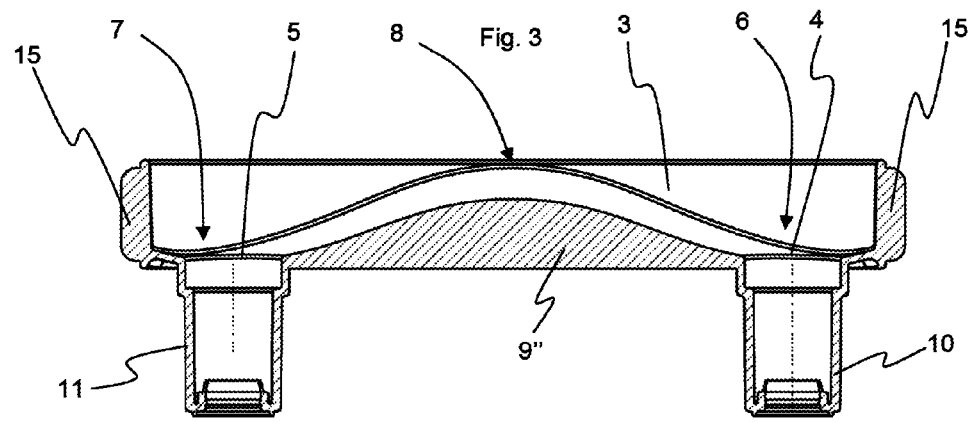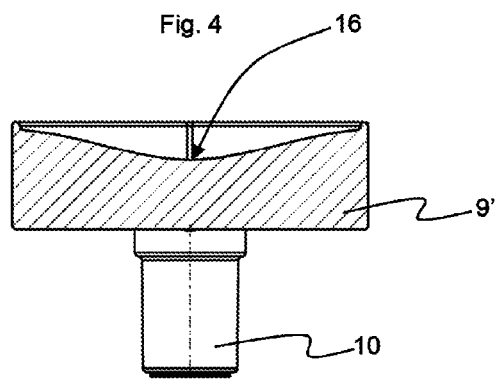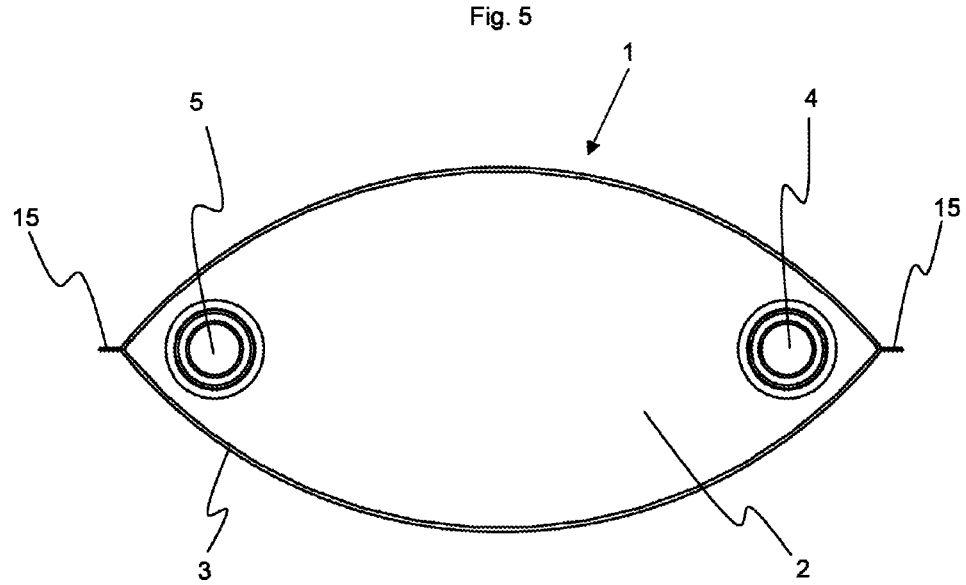

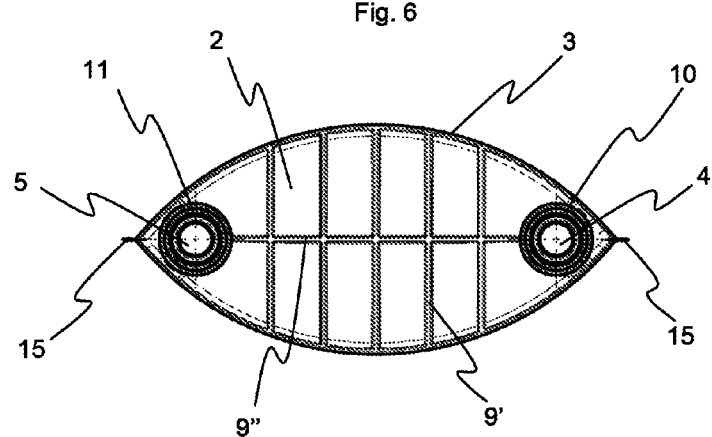
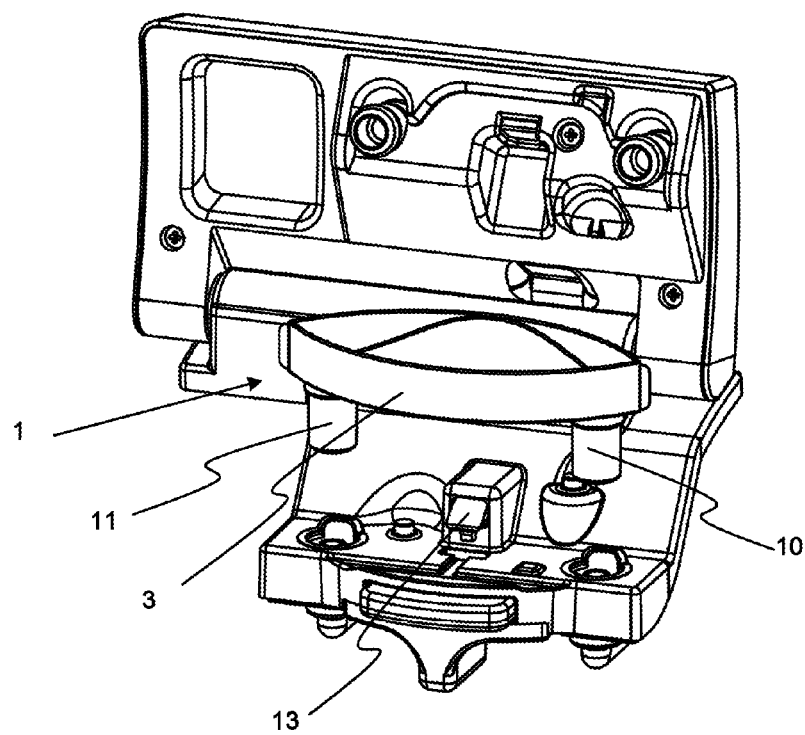

INSERT FOR RECEPTACLE CONTAINING SOLID PRODUCTS TO BE DISSOLVED

The invention concerns an insert for a receptacle containing a concentrated product in solid or liquid form, comprising a main part formed by a base extended on the edge by a wall perpendicular to the base, an opening being produced in the base. The invention also concerns a receptacle provided with an insert according to the invention.

Receptacle means either a flexible pouch, a cartridge, a bottle or any other container able to receive a concentrated liquid or solid and water or another liquid for solubilising or diluting this concentrate.

It is usual in haemodialysis to use dialysis solutions that are produced directly before the dialysis or even during it. For this purpose, haemodialysis machines are equipped with devices for producing these solutions. The pharmaceutical product is in the form of a concentrate, in general powders or granules contained in pouches or cartridges. These pouches or cartridges are connected to the dialysis machine, which introduces water into the receptacle and sucks out the solution thus produced.

The couplings are in some cases situated in the top of the receptacle, in other cases in the base of the receptacle. An example of a pouch provided with couplings in the base of the pouch is known from DE 101 52 105 A1. The couplings are situated approximately one third and two thirds of the way up from the base of the pouch, projecting inside the pouch. The drawback of this solution is that areas are formed that are not swept by the flow of water so that, at the end of the solubilisation procedure, remainders of salts accumulate in the base without their being entrained and solubilised by the water introduced into the receptacle.

From EP 1 084 691 A1, an insert is known, the head of which also projects into the receptacle. This insert consists of a main part in the form of a vessel. This main part consists of a flat base the periphery of which is extended by a perpendicular wall directed towards the external face of the base. This wall in the form of a vessel serves to weld the pouch. An opening is formed at the centre of the base, the said opening being extended on the external face by a tube. Transverse and longitudinal reinforcements are provided on the external face of the base. The tube continues on the internal face of the base in order to end up in a head element. The channel divides in the head element into two horizontal parts that emerge in the pouch well above the base. This insert therefore has the same drawbacks as those mentioned previously.

From EP 2 005 934 A2 an insert is known conforming to the preamble of the main claim. That insert is fixed to a sachet containing a medical solution ready for use. It has a flat bottom. A first opening is formed in this flat bottom. This opening is extended on the internal face of the insert by a tube. On the other side of the flat bottom there is a second opening extended on the external face of the insert by a second tube. The first opening is hermetically sealed by a plug that can be pierced by the needle of a standard transfusion device. Via the second opening it is possible on the one hand to introduce a "minor" component such as insulin and on the other hand to draw off the solution via another transfusion line. In the above document this second opening is therefore level with the flat bottom. However, because of this flat bottom, if it were used for containers containing solid products, this insert would not work in a satisfactory way. In fact, there would be a risk of the solid product accumulating on the flat bottom, notably between the two openings, behind the internal tube or in the corner at the edge of the bottom, on the side of the second opening. Moreover, the reinforcing ribs formed on the wall perpendicular to the bottom form crannies liable to retain the solid product.

The objective of the invention is therefore to develop an insert that makes it possible to empty the receptacle entirely.

This objective is achieved according to the invention because the face of the base intended to be situated in the receptacle after assembly, the so-called internal face, is concave at the opening so that the latter is situated at the bottom of a trough. In this way the formation of corners in which the liquid does not circulate, or not sufficiently, is prevented. The solid product cannot accumulate otherwise than in the trough so that it is always subjected to the flow of liquid.

To allow a continuous procedure, it is preferable to provide a second opening in the base. The internal face of the base at this second opening is preferably concave so that the second opening is also situated at the bottom of a trough.

In a favoured embodiment of the invention, the internal face of the base forms a wave so that each opening is situated in a trough separated from the other by the crest of the wave.

It is preferable for the wall to extend on the same side as the internal face of the base and/or on the same side as the opposite face, referred to as the external face. In the case of the favoured wave embodiment, the edge can fit flush with the external face of the base at the troughs of the wave and fit flush with the internal face at the crest of the wave, extending towards the internal face at the troughs and towards the external face at the crest.

In accordance with the invention, reinforcements fixed to the walls are provided on at least one of the faces of the base, preferably on the external face. This makes it possible to fabricate a hollow insert that is very light while being practically non-deformable.

In order to enable the receptacle provided with the insert to be coupled to a haemodialysis machine, it is preferable for the opening or at least one of the openings to be extended on the same side as the external face by a tube.

In a second variant embodiment of the invention, a reinforcement is fixed to the external face of the base extending as far as the two tubes, the reinforcement preferably being provided with locking means intended to cooperate with corresponding means on the taking-off machine and/or cross members perpendicular to the reinforcement.

To facilitate the welding of the pouch constituting the receptacle on the insert, it is preferable for the main part to be in the form of a vessel, each point of which is preferably extended by a tongue. In general, the receptacle is formed by a pouch produced by welding two strips on three sides, the fourth side being welded onto the insert. Thus the welds on the lateral edges end up by interposing the tongues and each base edge (the fourth edge) is welded on one side of the vessel, from one tongue to the other.

The invention is presented in more detail below with the help of the figures, which show:

FIG. 1: a perspective view from the side of the internal face of an insert according to the invention;

FIG. 2: a perspective view from the side of the external face of the insert of FIG. 1;

FIG. 3: a view in longitudinal section of the insert of FIG. 1;

FIG. 4: a view in transverse section of the insert of FIG. 1;

FIG. 5: a view from above of the insert of FIG. 1;

FIG. 6: a view from below of the insert of FIG. 1;

FIG. 7: a perspective view of a second embodiment of the insert according to the invention, the insert being mounted in the haemodialysis machine.

The insert according to the invention is intended for a pouch, a cartridge or any other suitable receptacle containing a product in powder or granule form having to be put in solution by a haemodialysis machine. It may also be a liquid that has to be diluted. The finished receptacle therefore consists of a container closed by the insert of the invention. In practice, the insert can be used in any other machine for putting in solution: although reference is always made hereinafter to a haemodialysis machine, it must be understood that the invention can be used for any other type of machine for putting in solution.

To allow putting in solution, the insert comprises at least one water inlet that can also serve as an outlet for the liquid. Preferably, the insert however comprises a water inlet and a distinct outlet for the solution produced in order to allow a continuous procedure. The example embodiments presented concern inserts provided with two openings. The following description can, however, be entirely adapted to an insert having only one opening, as will be shown below.

The insert according to the invention consists of a main body (1) formed by a base (2) extended over its periphery by a wall (3). The wall (3) serves essentially to weld the container, in particular the pouch or cartridge. Once fitted on a container, the insert therefore has an internal face and an external face. These spatial references are kept by analogy for the insert.

Two holes (4, 5) are produced in the base (2). Each hole (4, 5) is extended on the external face of the base (2) by a tube (10, 11). These tubes are intended to connect the insert to a haemodialysis machine. The dimensions and the relative positioning of the tubes are chosen according to the type of machine for which the insert is intended. For a machine of the Fresenius 5008 type for example, the separation between the axes of the two tubes is 72 mm, the diameter of the tubes 12.5 mm and the height thereof 9 mm. A porous filter is introduced into the openings and the tubes in order to prevent the solid product leaving the receptacle. These filters are for example produced from sintered polyethylene or micro-injected PE.

Contrary to the prior art, the base is not flat, but is in the shape of a wave. The first hole (4) is situated in a first trough (6), the second (5) in a second trough (7) of the wave, these two troughs (6, 7) being separated by the crest (8) of the wave. Considered from the side of the internal face, the base therefore has a concavity at each hole (4, 5). In the position of use in the haemodialysis machine, the holes (4, 5) constitute the lowest points on the internal face of the base (2) of the insert. The solid product therefore tends to fall into the troughs close to the openings and is thus always situated in the liquid flow, even when practically no more solid product remains.

In order to facilitate the welding of a pouch on the insert, the latter is in the form of a vessel, the crest of the wave being situated transversely to this vessel. The ends of the vessel are provided with tongues (15). The pouch is produced for example by means of two strips welded together on three of their sides, the fourth being welded to one of the faces of the wall (3) in the form of a vessel, from one tongue (15) to the other. Thus the base of the pouch is produced by the vessel-shaped insert, the lateral edges of the pouch starting directly from the insert without forming corners liable to be outside the flow of water. Nothing prevents the lateral walls of the pouch starting from the insert separating or approaching each other while moving away so that the pouch seen flat has the shape of a trapezium.

In the example presented in FIGS. 1 to 6, the wall (3) extends partly above and partly below the base (2). The troughs (6, 7) of the wave, that is to say at the ends of the vessel, the wall extends on the same side as the internal face of the base (2) while fitting flush with the external face of the base. On the other hand, at the crest of the wave (8), it extends on the same side as the external face of the base (2) while fitting flush with the internal face. It would however be entirely possible for the wall to extend only on one side of the base, the internal side or the external side, or even for it to extend on both sides while projecting beyond the two faces of the base.

In order to ensure better falling of the solid particles into the troughs (6, 7) close to the openings (4, 5), provision is made for the transverse section of the wave not to be flat but to have a trough (16), as shown by FIG. 4.

In the example in FIGS. 1 to 6, the external face of the main body (1) is hollow. To reinforce the main body and give it a certain rigidity, it is preferable to provide reinforcements (9) on the external face of the base (2). A longitudinal reinforcement (9') can be provided, extending from one tube (10) to the other (11), and transverse reinforcements (9") extending from one part of the wall to the other. These reinforcements (9) extend as far as the level of the free edge of the wall (3). Rather than providing a hollow main body, possibly reinforced, it would also have been possible to make it solid.

In a variant embodiment, not shown, the reinforcement consists of a single longitudinal rib (9') extending from one tube (10) to the other (11). A window is formed in this rib (9') to enable the receptacle to be locked in the haemodialysis machine. This locking is obtained with a lever (13) on the machine that snaps into the window and prevents the receptacle and insert unintentionally coming out of the machine. To ensure good vertical holding of the receptacle, two transverse ribs can be provided on each side of the window, one on each side of the longitudinal rib. They prevent the receptacle lying on the side.

The insert is produced for example by moulding in polyethylene or polypropylene.

Although the examples presented have two openings (4, 5), it is entirely possible for the insert to contain only one, or on the contrary more than two. In all cases, it is necessary for the openings to be situated at the base of a trough so that the remaining solid product tends to fall therein in order always to be subjected to the flow of liquid. It is preferable for the internal face of the bottom not to feature any flat place liable to form a horizontal plate on which the solid product could accumulate. The internal face of the bottom must therefore preferably feature only portions inclined towards the opening or openings, the inclined portions situated around a first hole and the inclined portions situated around a second hole meeting to form troughs or crests on which the solid product cannot accumulate.

By virtue of the insert of the invention, it is possible to produce pouches, cartridges or any other receptacle, without corners or dead spaces situated outside the flow of liquid. Thus all the solid product situated in the receptacle is situated in the flow and can be solubilised. The two openings being situated in the lowest points of the receptacle, all the liquid can be sucked out. Compared to a flat shape of the bottom of the insert, as known for example from EP 2 005 934 A2, positioning the hole or holes in cavities in the bottom, notably the wave shape between the two holes and its central concavity, enables better sliding of the solid materials and less disturbance to the flow because of the disappearance of a large portion of the crannies and corners. Similarly, during introduction of the solvent liquid, any solid materials that have accumulated in these cavities are entrained by the liquid, which promotes their dissolution.

The invention claimed is:

1. Insert for a receptacle for containing a concentrated product in solid or liquid form, said insert comprising a main part formed by (i) a base, and (ii) a side wall perpendicular to the base and extending over an edge of the base, so that the base forms a central wall transversal to the side wall, said central wall having a top face intended to be situated in the receptacle after assembly, called internal face, and a bottom face, called external face, opposed to the top face, wherein a first opening is provided in the central wall of the base, wherein a first area of the internal face located adjacent and surrounding the first opening is concave so as to form a first trough, the opening being situated at a bottom of the first trough.

2. Insert according to claim 1, wherein a second opening is provided in the central wall of the base.

3. Insert according to claim 2, wherein a second area of the internal face of the base located adjacent the second opening is concave, so that the second opening is situated at the bottom of a second trough.

4. Insert according to claim 3, wherein the internal face of the base forms a wave so that each of the first and second openings is situated in its respective trough separated from the other by a crest of the wave.

5. Insert according to claim 1, wherein the side wall extends on a same side as the internal face and on a same side as the external face of the central wall of the base.

6. Insert according to claim 1, wherein reinforcements fixed to the side wall are provided on at least one of the internal and external faces of the central wall of the base.

7. Insert according to claim 1, wherein the opening is extended on a same side as the external face by a tube.

8. Insert according to claim 2, wherein each of the first and second openings is extended on a same side as the external face by a respective tube, and wherein a reinforcement is fixed to the external face of a bottom while being extended as far as the two tubes.

9. Insert according to claim 1, wherein the main part is in the form of a vessel.

10. Receptacle for containing a concentrated product in solid or liquid form, comprising a container welded in its bottom part to the insert according to claim 1.

11. Insert according to claim 6, wherein the reinforcements fixed to the side wall are provided on the external face.

12. Insert according to claim 8, wherein the reinforcement is provided with locking means intended to cooperate with corresponding means on a take-off machine and/or cross members perpendicular to the reinforcement.

13. Insert according to claim 9, wherein the vessel has pointed ends, and each of the pointed ends is extended by a tongue.

14. Insert according to claim 2, wherein the side wall extends on a same side as the internal face and on a same side as the external face of the central wall of the base.

15. Insert according to claim 3, wherein the side wall extends on a same side as the internal face and on a same side as the external face of the central wall of the base.

16. Insert according to claim 4, wherein the side wall extends on a same side as the internal face and on a same side as the external face of the central wall of the base.

17. Insert according to claim 2, wherein reinforcements fixed to the side wall are provided on at least one of the internal and external faces of the central wall of the base.

18. Insert according to claim 3, wherein reinforcements fixed to the side wall are provided on at least one of the internal and external faces of the central wall of the base.

19. Insert according to claim 4, wherein reinforcements fixed to the side wall are provided on at least one of the internal and external faces of the central wall of the base.

20. Insert according to claim 5, wherein reinforcements fixed to the side wall are provided on at least one of the internal and external faces of the central wall of the base.

21. Insert according to claim 4, wherein a transverse section of the internal face at the crest forms a trough.

22. Insert according to claim 1, wherein the first trough surrounding the first opening extends to the edge of the base.

* * * * *